United States Patent [19]

Yagihara et al.

[11] 4,254,212
[45] Mar. 3, 1981

[54] PHOTOGRAPHIC SILVER HALIDE LIGHT-SENSITIVE MATERIAL AND COLOR IMAGE-FORMING PROCESS

[75] Inventors: Morio Yagihara; Yukio Yokota; Akira Ogawa, all of Minami-ashigara; Hiroshi Sawaguchi, Odaware, all of Japan

[73] Assignee: Fuji Photo Film Co., Ltd., Ashigara, Japan

[21] Appl. No.: 70,544

[22] Filed: Aug. 29, 1979

[30] Foreign Application Priority Data

Aug. 29, 1978 [JP] Japan .................................. 53/105197

[51] Int. Cl.³ ................................................ G03C 1/40
[52] U.S. Cl. ..................................... 430/381; 430/384; 430/385; 430/548; 430/552; 430/553
[58] Field of Search .............. 430/384, 385, 381, 552, 430/553, 359, 548, 362

[56] References Cited

U.S. PATENT DOCUMENTS 4,052,212 10/1977 Deguchi ............................ 430/385
4,141,730 2/1979 Minagawa ......................... 430/359

FOREIGN PATENT DOCUMENTS 1440126 6/1976 United Kingdom ................... 430/553

*Primary Examiner*—Mary F. Downey
*Attorney, Agent, or Firm*—Sughrue, Rothwell, Mion, Zinn and Macpeak

[57] ABSTRACT

A photographic silver halide light-sensitive emulsion containing a cyan color forming colorless coupler having at the coupling position at which the coupler reacts with the oxidation product of an aromatic primary amine developing agent at least one alkoxy group having a sulfonyl group as a substituent and represented by the following general formula (I):

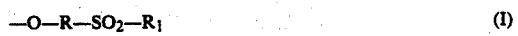

$$-O-R-SO_2-R_1 \qquad (I)$$

wherein R represents a saturated or unsaturated divalent aliphatic group having 1 to 4 carbon atoms which may be straight or branched chain and may be substituted (except those having an aryl group as a substituent on the carbon atom adjacent the oxygen atom bonded to the coupling position); and $R_1$ represents an aliphatic group, an aromatic group or a heterocyclic group; and wherein R and $R_1$ can combine directly or through a bonding group to form a ring and an image-forming process.

36 Claims, No Drawings

PHOTOGRAPHIC SILVER HALIDE LIGHT-SENSITIVE MATERIAL AND COLOR IMAGE-FORMING PROCESS

BACKGROUND OF THE INVENTION

1. Field of the Invention

The present invention relates to a photographic color coupler and particularly to a novel 2-equivalent cyan coupler, to a color photographic light-sensitive material containing such a photographic coupler, and to a method of forming images using such a photographic coupler.

2. Description of the Prior Art

As is well known in the art, color images can be formed by imagewise exposure of a silver halide photographic light-sensitive material followed by color development whereby the oxidation product of the aromatic primary amine developing agent reacts with a dye forming coupler.

Generally speaking, this color image method is based on the subtractive color reproduction principle, with cyan, magenta and yellow color images, each of which is in a complementary relationship to red, green and blue light, respectively, being produced. For example, cyan dye images are generally produced from couplers comprising phenol or naphthol derivatives. In the color photographic method, a color forming coupler added to a developer solution or incorporated in a light-sensitive photographic emulsion layer or other color image forming layer reacts with the oxidation product of a color developing agent which is formed upon development to provide a non-diffusible dye. The reaction between the coupler and the color developing agent takes place at the active sites of the coupler. One mol of a so-called "four-equivalent coupler" in which all of the active sites are substituted with hydrogen atoms theoretically requires on a stoichiometric basis 4 mols of silver halide having developing nuclei as an oxidizing agent to form 1 mol of a dye. On the other hand, 2-equivalent couplers are known which have substituents releasable as anions at the active sites and which require only 2 mols of silver halide having developing nuclei. Accordingly, by use of 2-equivalent couplers, the amount of silver halide in the light-sensitive layer can be generally reduced and, hence, the coating thickness thereof can be reduced. This, in turn, enables the processing time of the light-sensitive material to be decreased and simultaneously results in the sharpness of the resulting color images being advantageously improved.

A variety of such coupling releasable groups are known including, for example, the sulfonamido groups set forth in U.S. Pat. No. 3,737,316, the imido groups set forth in U.S. Pat. No. 3,749,735, the sulfonyl groups set forth in U.S. Pat. No. 3,622,328, the aryloxy groups set forth in U.S. Pat. No. 3,476,563, the acyloxy groups set forth in U.S. Pat. No. 3,311,476, the thiocyano groups set forth in U.S. Pat. No. 3,214,437, the isothiocyanato groups set forth in U.S. Pat. No. 4,032,345, the sulfonyloxy groups set forth in U.S. Pat. No. 4,046,573, the thiocarbonyloxy groups set forth in Japanese Patent Application (OPI) No. 51939/1977 (The term "OPI" as used herein refers to a "published unexamined Japanese patent application"), the aralkenylcarbonyloxy groups set forth in Japanese Patent Application (OPI) Nos. 39126/1978 and 39745/1978, the S-substituted monothiocarbonyloxy groups set forth in Japanese Patent Application (OPI) No. 45524/1978, the propionyloxy groups set forth in Japanese Patent Application (OPI) No. 47827/1978, the

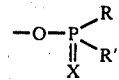

groups set forth in U.S. Pat. No. 4,072,525, and the substituted alkoxy groups set forth in U.S. Pat. Nos. 3,227,551, 4,052,212, 4,134,766 and 4,146,396, Japanese Patent Application (OPI) Nos. 120334/1975 and 105226/1978, French Pat. No. 2,321,715 and German Patent Application (OLS) No. 2,805,707.

Further, if the coupler contains a suitable type of coupling releasable group, for example, one which forms a diffusible dye structure, such a coupler, referred to as a diffusible dye releasing coupler, can be employed in a diffusion transfer process in which the released dye is used to provide a dye image in an image receiving layer. Diffusible dye releasing couplers are described in, for example, U.S. Pat. Nos. 3,227,550, 3,765,886, U.S. Defensive Publication No. T900,029, British Pat. No. 1,330,524, etc. In addition, certain 2-equivalent colored couplers exhibit a masking effect to correct undesirable absorptions of dyes as described in, for example, British Pat. No. 1,501,743.

Furthermore, 2-equivalent couplers releasing a compound having a development suppressing effect, which are referred to as development inhibitor releasing couplers, are known. Since these couplers can suppress or inhibit development in proportion to the amount of the developed silver, these couplers are quite effective in improving image graininess, gradation control as well as improving color reproduction characteristics. These couplers can also be used in a diffusion transfer process because they affect a layer adjacent to the layer in which they are present. Examples of these couplers are described in U.S. Pat. Nos. 3,227,554 and 3,933,500.

Since a 2-equivalent coupler has essential advantages and a wider range of applications as compared with a 4-equivalent coupler, the photographic industry tends to use the 2-equivalent coupler more frequently.

However, most known 2-equivalent cyan color forming couplers have certain disadvantages in that the coupling reactivity is insufficient, in that remarkable color fog is formed, in that the dispersion property is poor which causes difficulties during coating, in that the compound per se is unstable and cannot be stored for a long time, in that the storage stability of the resulting color image after color development is poor, etc. The improvement of these disadvantages has been desired.

SUMMARY OF THE INVENTION

The first object of the present invention is to provide a new class of 2-equivalent cyan color forming couplers free from the above-described disadvantages and having an extremely good color forming property.

A second object of the present invention is to provide a method of forming cyan color image through development of a silver halide photographic emulsion in the presence of a new class of 2-equivalent coupler.

A third object of the present invention is to provide a silver halide color photographic light-sensitive material containing a new class of couplers and to provide a method of photographic processing using such as photographic material.

A fourth object of the present invention is to provide a means for improving in the sharpness of resulting color images by the reduction of the amount of silver halide in the photographic emulsion due to the use of a new class of couplers.

A fifth object of the present invention is to provide a 2-equivalent coupler which can form color images having a good spectral absorption property and an excellent stability to heat and high humidity for a long time.

A sixth object of the present invention is to provide a new class of couplers which can form color images having high sensitivity, high gamma and high density upon color development.

It has now been found, after extensive investigation, that the above cited objects of this invention are achieved by using a colorless photographic cyan color forming coupler having at the coupling position at which the coupler reacts with the oxidation product of an aromatic primary amine developing agent, as a coupling off group, at least one alkoxy group substituted with a sulfonyl group represented by the following general formula (I):

$$-O-R-SO_2-R_1 \quad (I)$$

wherein R represents a saturated or unsaturated, divalent aliphatic group having 1 to 4 carbon atoms which may be straight or branched chain and may be substituted (for example, by a halogen atom or a phenyl group) in addition to the sulfonyl group (provided R is not substituted with an aryl group at the α-position); and $R_1$ represents an aliphatic group, an aromatic group or a heterocyclic group; and wherein R and $R_1$ can combine directly or through a connecting group to form a ring.

DETAILED DESCRIPTION OF THE INVENTION

The group represented by the general formula (I) above splits off when a cyan dye is formed by the coupling reaction.

The term "colorless" couplers as used herein means those couplers whose molecular extinction coefficient at the absorption maximum thereof does not exceed 5,000 within the visible spectrum.

The colorless 2-equivalent cyan color forming coupler of the present invention exhibits a higher rate of dye formation than prior art couplers containing an alkoxy group mainly due to the coupling-off groups. As a result a photographic material using the colorless cyan color forming coupler has a high photographic speed, gradation and maximum density when processed using not only conventional processing but also using a rapid processing. The coupler of the present invention shows a low tendency to fog and color stain formation in a light-sensitive layer, and moreover, has excellent dispersibility in a photographic layer such as a light-sensitive layer of a photographic light-sensitive material at higher content levels. Further, the cyan dyes resulting from this type of cyan coupler have a superior fastness to light, heat and humidity, and an excellent light-absorbing property free from undesired spectral absorption.

Furthermore, the coupler of the present invention has an advantage that it is useful for an image forming coupler in a conventional system.

Preferred couplers of the present invention are couplers represented by the following general formula (Ia) and symmetric or asymmetric couplers represented by the following general formula (Ib):

$$A(O-R-SO_2-R_1)_n \quad (Ia)$$

$$A-O-R-SO_2-R'-O-A' \quad (Ib)$$

In the formulae (Ia) and (Ib), A represents a cyan color forming coupler residue having a naphthol nucleus or a phenol nucleus; and A' represents a cyan color forming coupler residue having a naphthol nucleus or a phenol nucleus which may be the same as A or different.

R and R' each represents an alkylene group having 1 to 4 carbon atoms, or a saturated or unsaturated divalent aliphatic group having 1 to 4 carbon atoms (for example, methylene, dimethylene, trimethylene, 2n-methyldimethylene, 2-methyltrimethylene, etc.). The divalent aliphatic group may be straight chain or branched chain and may also be substituted with one or more substitutents other than the sulfonyl group. Examples of the substituents include a halogen atom or a substituted or unsubstituted aryl group or a sulfonyl group. (However, R and R' each is not substituted with an aryl group at the α-position.) Further, R and R' may be the same or different.

$R_1$ represents an alkyl group having 1 to 18 carbon atoms, an alkenyl group having 1 to 18 carbon atoms, an aralkyl group having 6 to 12 carbon atoms, an aralkenyl group having 6 to 12 carbon atoms, an aryl group having 6 to 12 carbon atoms, which may be mono- or bicyclic aryl group, or a 5-membered 6-membered heterocyclic group containing a nitrogen atom, which may further contain an oxygen atom, a sulfur atom and/or a nitrogen atom.

Suitable examples of the alkyl group represented by $R_1$ include a methyl group, an ethyl group, an n-propyl group, an isopropyl group, an n-butyl group, a t-butyl group, an n-hexyl group, an n-octyl group, an n-dodecyl group, an n-octadecyl group, etc.

Suitable examples of the alkenyl group represented by $R_1$ include a butenyl group, a tridecenyl group, etc.

Suitable examples of the aralkyl group represented by $R_1$ include a benzyl group, a phenylethyl group, etc.

Suitable examples of the aralkenyl group represented by $R_1$ include a phenylbutenyl group, etc.

Suitable examples of the aryl group represented by $R_1$ include a phenyl group, a tolyl group, a naphthyl group, etc.

Suitable examples of the heterocyclic group represented by $R_1$ include a triazolyl group, a tetrazolyl group, an imidazolyl group, a pyrazolyl group, a thiazolyl group, a piperazyl group, etc.

The alkyl group, the alkenyl group, the aralkyl group, the aralkenyl group, the aryl group and the heterocyclic group represented by $R_1$ may be substituted with a halogen atom (for example, fluorine, chlorine, or bromine), a nitro group, a cyano group a hydroxy group, an alkoxy group, an acyloxy group, an acylamino group, a sulfonamido group, a sulfamoyl group, a sulfonyl group, a carboxy group or a sulfo group, etc., or other substituents. Further, the alkyl group, the alkenyl group, the aralkyl group and the aralkenyl group represented by $R_1$ may be straight chain or branched chain.

The most preferred positions for substitution of the sulfonyl group on the splittable alkoxy group in the general formulae (Ia) and (Ib) are the α-, β- and γ-positions of the alkoxy group R.

n represents a positive integer. Although the preferred value for n is 1 or 2, n can have a value of 3 or more up to the number of coupling active positions in the molecule if, for example, the cyan coupler comprises a polymerized coupler.

The cyan coupler residue in the structure shown by the general formula (Ia) above is the part remaining after removal of the hydrogen atoms or coupling-off groups from the active sites of the cyan coupler. Where plural active sites are present in the same coupler molecule, the coupling-off groups, including hydrogen atoms, substituted at these active sites may be the same or different. More preferably, however, all active positions of the coupler should be substituted with coupling-off groups in accordance with the present invention.

Of the couplers of the present invention, the most useful couplers are represented by either of the following general formulae (IIA) and (IIB):

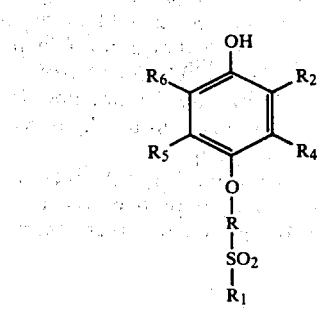

(IIA)

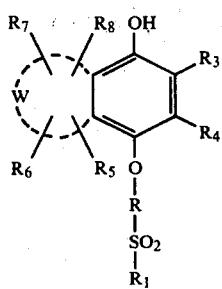

(IIB)

In the general formulae (IIA) and (IIB), R and $R_1$ each has the same meaning as R and $R_1$ defined in the general formula (I).

$R_2$ represents a hydrogen atom, an aliphatic group containing up to 30 carbon atoms (e.g., an alkyl group containing up to 30 carbon atoms such as methyl, isopropyl, pentadecyl, eicosyl, etc.), an alkoxy group containing up to 30 carbon atoms (e.g., methoxy, isopropoxy, pentadecyloxy, eicosyloxy, etc.), an aryloxy group having 6 to 30 carbon atoms (e.g., phenoxy, p-tert-butylphenoxy, etc.), an acylamido group, a sulfonamido group, a phosphoramido group or a ureido group, each represented by one of the following general formulae (III) to (VI), or a carbamoyl group represented by the general formulae (VII) or (VIII):

—NH—CO—B (III)

—NH—SO$_2$—B (IV)

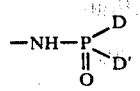

(V)

—NHCONH—B (VI)

—CONH—B (VII)

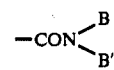

(VIII)

B and B' in the general formulae (III) to (VIII) above, which may be the same or different, each represents an aliphatic group containing 1 to 32 carbon atoms (preferably a straight chain or branched chain alkyl group containing 1 to 20 carbon atoms or a cyclic alkyl group having 3 to 32 carbon atoms, preferably 3 to 20 carbon atoms (for example, cyclopropyl, cyclohexyl, norbornyl, etc.), or a mono- or bicyclic aryl group having 6 to 32 carbon atoms, preferably 6 to 20 carbon atoms (for example, phenyl, naphthyl, etc.). The alkyl group and the aryl group described above may be substituted with one or more of a halogen atom (for example, fluorine, chlorine, etc.), a nitro group, a cyano group, a hydroxyl group, a carboxy group, an amino group (for example, an amino group, an alkylamino group, a dialkylamino group, an anilino group, an N-alkylanilino group, etc.), an alkyl group (such as those described above), an aryl group having 1 to 20 carbon atoms (for example, phenyl, acetylaminophenyl, etc.), an alkoxycarbonyl group having 1 to 20 carbon atoms (for example, tetradecyloxycarbonyl, etc.), an acyloxycarbonyl group, an amido group (for example, acetamido, methanesulfonamido, etc.), an imido group (for example, succinimido, etc.), a carbamoyl group (for example, N,N-dihexylcarbamoyl, etc.), a sulfamoyl group (for example, N,N-diethylsulfamoyl, etc.), an alkoxy group having 1 to 20 carbon atoms (for example, ethoxy, tetradecyloxy, octadecyloxy, etc.), an aryloxy group having 6 to 20 carbon atoms (for example, phenoxy, p-tert-butylphenoxy, 2,4-diamylphenoxy, 4-hydroxy-3-tert-butylphenoxy, etc.), etc. D and D' each represents the group described above for B and additionally an —OB group, an —NH—B group or an —NB$_2$ group.

$R_3$ is a hydrogen atom, an aliphatic group containing up to 30 carbon atoms, more preferably an alkyl group having 1 to 20 carbon atoms or a carbamoyl group represented by the formulae (VII) and (VIII) described above. $R_4$, $R_5$, $R_6$, $R_7$ and $R_8$ each represents a hydrogen atom, a halogen atom, an alkyl group, an aryl group, an alkoxy group, an alkylthio group, a heterocyclic ring, an amino group, a carbonamido group, a sulfonamido group, a sulfamyl group or a carbamyl group. For example, $R_4$ may represent the following groups:

a hydrogen atom; a halogen atom (for example, chlorine, bromine, etc.); a primary, secondary or tertiary alkyl group having 1 to 22 carbon atoms, which may be straight or branched chain (for example, methyl, propyl, isopropyl, n-butyl, sec-butyl, tert-butyl, hexyl, dodecyl, 2-chlorobutyl, 2-hydroxyethyl, 2-phenylethyl, 2-(2,4,6-trichlorophenyl)ethyl, 2-aminoethyl, etc.); a cyclic alkyl group having 3 to 22 carbon atoms; a straight or branched chain alkylthio group having 1 to 20 carbon atoms (for example, hexadecylthio, etc.); a cyclic alkylthio group having 3 to 20 carbon atoms; a mono- or bicyclic aryl group having 6 to 20 carbon atoms (for example, phenyl, 4-methylphenyl, 2,4,6-trichlorophenyl, 3,5-dibromophenyl, 4-trifluoromethylphenyl, 2-trifluoromethylphenyl, 3-trifluoromethylphenyl, naphthyl, 2-chloronaphthyl, 3-ethylnaphthyl, etc.);

a 5-membered or 6-membered heterocyclic group containing a nitrogen atom, an oxygen atom and/or a sulfur atom, which may be a mono- or bicyclic group (for example, benzofuranyl, furanyl, thiazolyl, benzothiazolyl, naphthothiazolyl, oxazolyl, benzoxazolyl, naphthoxazolyl, pyridyl, quinolinyl, etc.); an amino group containing an unsubstituted amino group, a straight or branched chain alkylamino group having 1 to 20 carbon atoms, a cyclic alkylamino group having 3 to 20 carbon atoms, a mono- or bicyclic arylamino group having 6 to 20 carbon atoms or a heterocyclic amino group (for example, amino, methylamino, diethylamino, dodecylamino, phenylamino, tolylamino, 4-(3-sulfobenzamido)-anilino, 4-cyanophenylamino, 2-trifluoromethylphenylamino, benzothiazolylamino, etc.); a carbonamido group (for example, a straight or branched alkylcarbonamido group having 1 to 20 carbon atoms such as ethylcarbonamido, dodecylcarbonamido, etc., a cyclic alkylcarbonamido group having 3 to 20 carbon atoms such as phenylcarbonamido, etc.; a mono- or bicyclic arylcarbonamido group having 6 to 20 carbon atoms such as phenylcarbonamido, 2,4,6-trichlorophenylcarbonamido, 4-methylphenylcarbonamido, 2-ethoxyphenylcarbonamido, 3-[α-(2,4-ditert-amylphenoxy)acetamido]benzamido, naphthylcarbonamido, etc.; a 5-membered or 6-membered heterocyclic carbonamido group containing a nitrogen atom, an oxygen atom or a sulfur atom, which may be a mono- or bicyclic group such as thiazolylcarbonamido, benzothiazolylcarbonamido, naphthothiazolylcarbonamido, oxazolylcarbonamido, benzoxazolylcarbonamido, imidazolylcarbonamido, benzimidazolylcarbonamido, etc.); a sulfonamido group (for example, a straight or branched alkylsulfonamido group having 1 to 20 carbon atoms such as butylsulfonamido, dodecylsulfonamido, etc., a cyclic alkylsulfonamido group having 3 to 20 carbon atoms such as phenylsulfonamido, etc.; a mono- or bicyclic arylsulfonamido group having 6 to 20 carbon atoms, such as phenylsulfonamido, 2,4,6-trichlorophenylsulfonamido, 2-methoxyphenylsulfonamido, 3-carboxyphenylsulfonamido, naphthylsulfonamido, etc.; a 5-membered or 6-membered heterocyclic sulfonamido group containing a nitrogen atom, an oxygen atom or a sulfur atom, which may be mono- or bicyclic group such as thiazolylsulfonamido, benzothiazolylsulfonamido, imidazolylsulfonamido, benzimidazolylsulfonamido, pyridylsulfonamido, etc.); a sulfamyl group (for example, a straight or branched alkylsulfamyl group having 1 to 20 carbon atoms such as propylsulfamyl, octylsulfamyl, pentadecylsulfamyl, octadecylsulfamyl, etc., a cyclic alkylsulfamyl group having 3 to 20 carbon atoms; a mono- or bicyclic arylsulfamyl group having 6 to 20 carbon atoms such as phenylsulfamyl, 2,4,6-trichlorophenylsulfamyl, 2-methoxyphenylsulfamyl, naphthylsulfamyl, etc.; a 5-membered or 6-membered heterocyclic sulfamyl group containing a nitrogen atom, an oxygen atom or a sulfur atom, which may be a mono- or bicyclic group such as thiazolylsulfamyl, benzothiazolylsulfamyl, oxazolylsulfamyl, benzimidazolylsulfamyl, pyridylsulfamyl, etc.); and a carbamyl group (for example, a straight or branched alkylcarbamyl group having 1 to 20 carbon atoms such as ethylcarbamyl, octylcarbamyl, pentadecylcarbamyl, octadecylcarbamyl, etc., a cyclic alkylcarbamyl group having 3 to 20 carbon atoms; a mono- or bicyclic arylcarbamyl group having 6 to 20 carbon atoms such as phenylcarbamyl, 2,4,6-trichlorophenylcarbamyl, etc., and a 5-membered or 6-membered heterocyclic carbamyl group containing a nitrogen atom, an oxygen atom or a sulfur atom, which may be a mono- or bicyclic group such as thiazolylcarbamyl, benzothiazolylcarbamyl, oxazolylcarbamyl, imidazolylcarbamyl, benzimidazolylcarbamyl, etc.). Specific examples for $R_5$, $R_6$, $R_7$ and $R_8$ include those described above for $R_4$, while W represents the non-metallic atomic group necessary to complete a 5-membered or 6-membered saturated or unsaturated carbocyclic ring or a 5-membered or 6-membered saturated or unsaturated heterocyclic ring containing a nitrogen atom, an oxygen atom and/or a sulfur atom such as a benzene ring, a cyclohexene ring, a cyclopentene ring, a thiazole ring, an oxazole ring, an imidazole ring, a pyridine ring, a pyrrole ring, etc., the most preferred ring formed by W is a benzene ring.

The coupling-off group particularly suitable for the coupler represented by the general formulae (IIA) or (IIB) hereinabove is that represented by the formula $-O-R-SO_2-R_1$ wherein R has the same meaning as defined in the general formula (Ia) above, and $R_1$ represents an alkyl group having 1 to 18 carbon atoms which is unsubstituted or substituted by the substituent groups for the group $R_1$ of the general formula (Ia) or a phenyl group having at least one carboxyl group, hydroxy group, sulfo group or sulfamyl group.

Representative examples of the coupler of the present invention are set forth below, but the present invention should not be construed as being limited to these examples.

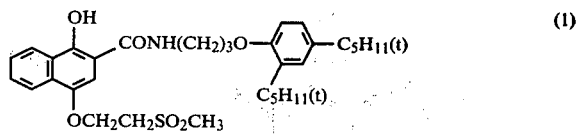

(1)

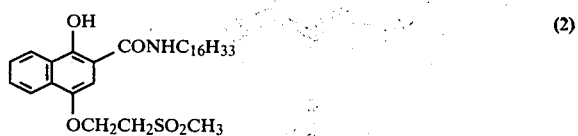

(2)

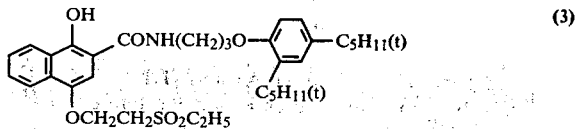

(3)

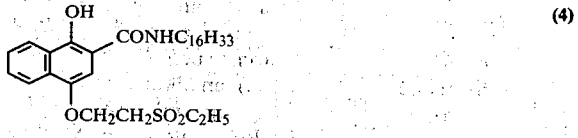

(4)

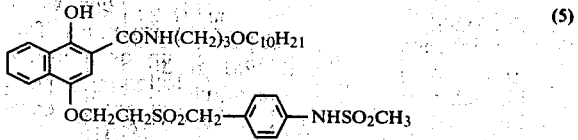

(5)

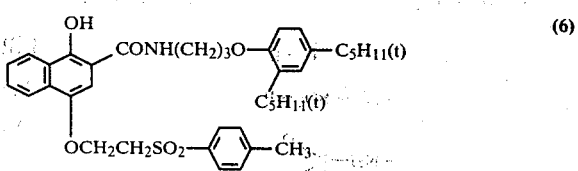

(6)

-continued
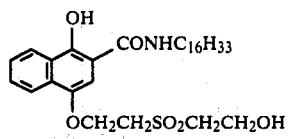 (7)
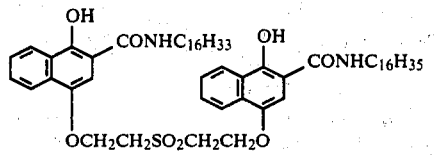 (8)
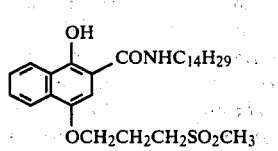 (9)
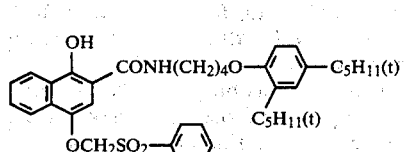 (10)
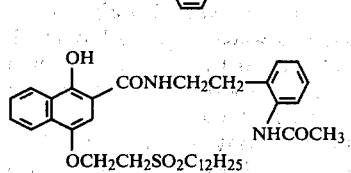 (11)
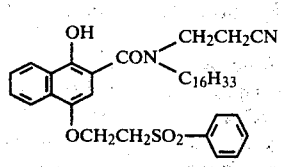 (12)
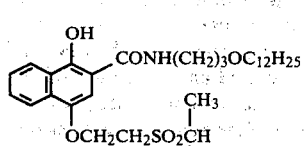 (13)
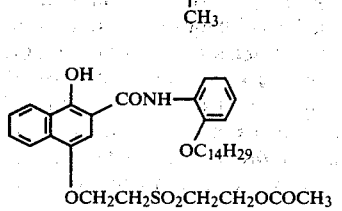 (14)
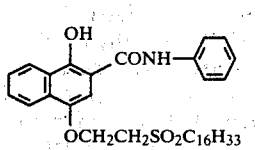 (15)
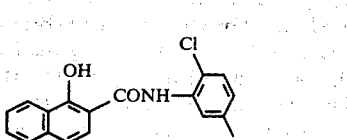 (16)
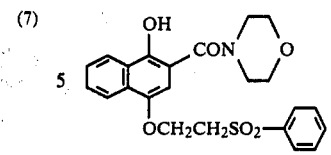 (17)
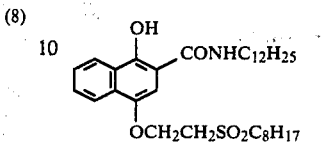 (18)
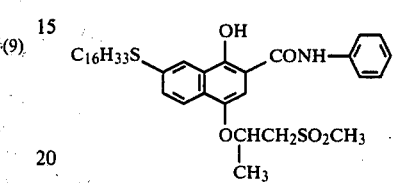 (19)
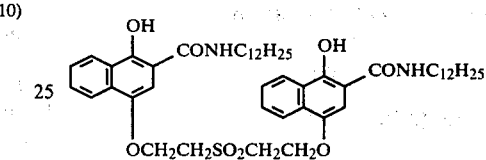 (20)
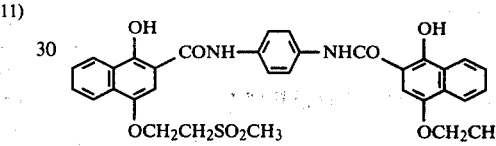 (21)
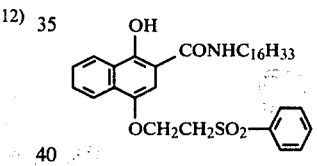 (22)
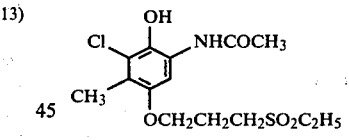 (23)
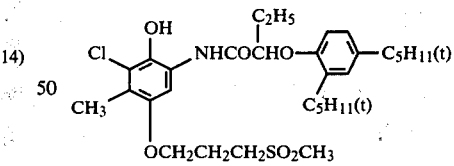 (24)
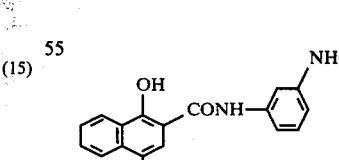 (25)
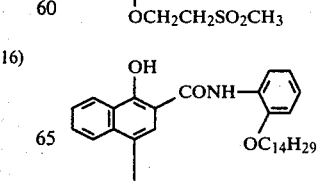 (26)

-continued

(27) 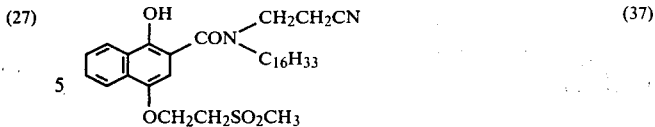

(28)

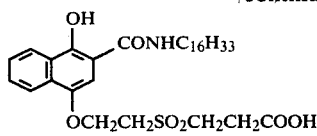

(29)

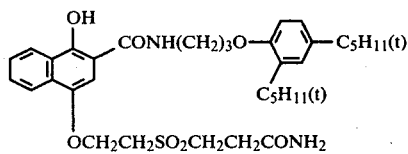

(30)

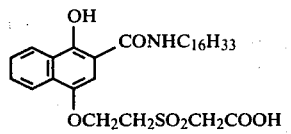

(31)

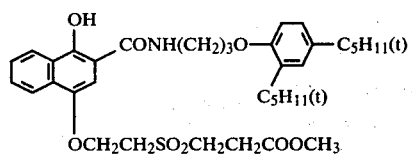

(32)

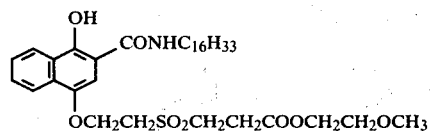

(33)

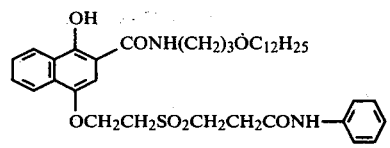

(34)

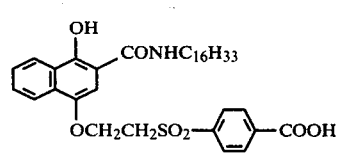

(35)

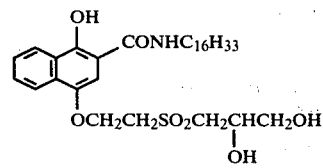

(36)

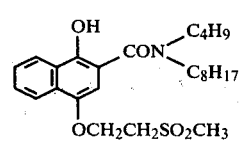

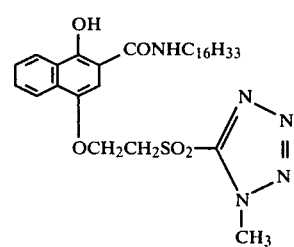

The compounds according to the present invention can be synthesized using the following procedures.

In the case of a naphthol type compound, the synthesis thereof can be made as follows.

(a) 1,4-dihydroxy-2-naphthoic acid can be reacted with an alkyl halide having a sulfonyl group as a substituent in a solvent such as acetone, dimethylformamide (DMF), water, methanol, etc., in the presence of pyridine, sodium carbonate, sodium hydroxide, a sodium alkoxide, etc., at about 35° to about 60° C. at a pH of more than 10. Usually, the reaction can be carried out using about 2 to 2.5 mols of an alkyl halide per mol of 1,4-dihydroxy-2-naphthoic acid, further using about 5 ml of a solvent per g of 1,4-dihydroxy-2-naphthoic acid in an atmosphere of $N_2$ gas.

(b) Alternatively, the introduction of an alkoxy group having a sulfonyl group at the β-position can be carried out in the following manner. For example, 1,4-dihydroxy-2-naphthoic acid can be reacted with a vinyl sulfone in a solvent such as water, methanol, ethanol, etc., in the presence of sodium hydroxide, a solution alkoxide, etc., at about 50° to about 100° C. at a pH of more than 10. Usually, the reaction can be carried out using about 2 to 4 mols of a vinyl sulfone per mol of 1,4-dihydroxy-2-naphthoic acid, further using about 5 ml of a solvent per g of 1,4-dihydroxy-2-naphthoic acid in an atmosphere of $N_2$ gas.

(c) 1,4-dihydroxy-2-naphthoic acid can be reacted with an alcohol having a sulfonyl group as a substituent in a solvent such as anisole, xylene, toluene, etc., in the presence of an acid catalyst such as sulfonic acid, p-toluenesulfonic acid or methanesulfonic acid at about 100° to about 150° C. The reaction can proceed advantageously using about 2 to about 4 mols of alcohol per mol of 1,4-dihydroxy-2-naphthoic acid and 10 ml of solvent per g of 1,4-dihydroxy-2-naphthoic acid in the presence of about 0.6 to about 1.0 mol of the acid catalyst per mol of 1,4-dihydroxy-2-naphthoic acid to obtain a 1-hydroxy-4-substituted alkoxy-2-naphthoic acid compound. Of the above three processes the process (c) is preferred. The compound is then converted into the acid chloride or into the phenyl ester using conventional methods, which is then subjected to a condensation with an amine, such as, for example, aniline, 2,4-di-tert-amylphenoxypropylamine, etc., to prepare the coupler.

In the case of a phenol type coupler, after the hydroxy group at the 1-position of the 1,4-dihydroxybenzene compound has been protected by, for example, pyranyl etherification, or after the 1-hydroxy group and the 2-acetylamino group of the 1,4-dihydroxybenzene compounds are mutually reacted to form an oxazole ring using the method described in Japanese Patent Application (OPI) No. 153923/1977, the compound is subjected to an alkylation of the 4-hydroxy group with an appropriate alkyl halide having a sulfonyl group as a substituent in a solvent such as methanol, ethanol, acetone, dimethylformamide (DMF), etc., in the presence of an alkali catalyst such as potassium carbonate, sodium methoxide, sodium ethoxide, etc., at about 60° to about 85° C. Usually, the reaction can be carried out using about 1.5 to about 2 mols of the alkyl halide per mol of 1,4-dihydroxybenzene compound, further using about 1.5 to 2 mols of the alkali catalyst per mol of 1,4-dihydroxybenzene compound. Then, the oxazole ring is cleaved with an acid and the compound thus-obtained is reacted with an appropriate acid chloride in the presence of a dehydrochlorinating agent to obtain the coupler.

Also, in case of a phenolic type or a naphtholic type compound, a 1,4-dihydroxyaryl compound represented by the following general formulae (IX) or (X):

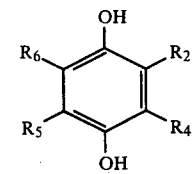

(IX)

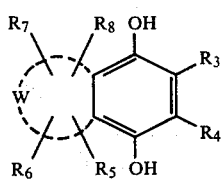

(X)

wherein $R_2$, $R_3$, $R_4$, $R_5$, $R_6$, $R_7$, $R_8$ and W each has the same meaning as defined in the general formulae (IIA) or (IIB), can be reacted with an appropriate alkyl halide or an appropriate alcohol under the reaction conditions described above to obtain the coupler.

Furthermore, the coupler can be synthesized by conducting the reaction as shown in the following equation:

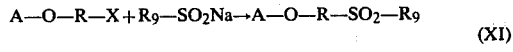

(XI)

wherein A and R each has the same meaning as defined in the general formula (Ia); X represents a halogen atom (chlorine or bromine); and $R_9$ represents an aryl group or an alkyl group, under the conditions described in R. Otto, Ber. Deut. Chem. Ges., 13, 1272 (1880), Ann. Chem., 283 181 (1894), E. Fromm and J. de Seixas Palma, Ber. Deut. Chem. Ges., 39, 3308 (1906) and R.L. Shriner, H.C. Struck, and W.J. Jorison, J. Amer. Chem. Soc., 52, 2067 (1930).

As the above examples of the coupler indicate, very often the coupler residue A includes other substitution. In the case of phenol and naphthol type couplers, this substitution is introduced before or after introducing the coupling-off group depending upon whether the conditions for the introduction of the coupling-off group affect the other positions of the coupler residue. In particular, in the case of an ester substituent, since the conditions used to introduce the coupling-off group generally affect the ester group, it is better to introduce the ester group or similar substituents after introduction of the coupling-off group. With regard to phenol type couplers that contain an acylamino group at the 2-position, in particular, the oxazole ring method described in Japanese Patent Application (OPI) No. 153923/1977 is advantageous.

Representative examples of the synthesis of couplers according to the present invention are described below.

SYNTHESIS EXAMPLE 1

Synthesis of 1-Hydroxy-4-(β-ethylsulfonylethoxy)-N-[γ-(2,4-di-tert-amylphenoxy)propyl]-2-naphthamide: Coupler (3)

20.4 g (0.1 mol) of 1,4-dihydroxy-2-naphthoic acid and 19 g (0.1 mol) of p-toluenesulfonic acid were added to 200 ml of dehydrated toluene. To the mixture, 27.6 g (0.2 mol) of β-ethylsulfonylethanol was added dropwise for 30 minutes under heating at 95° C. with stirring. After heating with stirring for 7 hours, the mixture was cooled to 20° to 30° C. 100 ml of acetonitrile was added to the mixture, the solid deposited was separated by filtration to obtain 17.2 g (53%) of 1-hydroxy-4-(β-ethylsulfonylethoxy)-2-naphthoic acid.

13 g (0.04 mol) of the naphthoic acid derivative thus obtained, 4.5 g (0.048 mol) of phenol and 4.0 ml of dimethylformamide were added to 100 ml of acetonitrile. To the mixture, 9.18 g (0.06 mol) of phosphorus oxychloride was added dropwise under heating with stirring. After heating with stirring for 3 hours, acetonitrile was removed under reduced pressure. 100 ml of methanol was added to the mixture, the crystals deposited were collected by filtration to obtain 11.4 g (71%) of phenyl ester of 1-hydroxy-4-(β-ethylsulfonylethoxy)-2-naphthoic acid.

10 g (0.025 mol) of the phenyl ester thus obtained was added to 50 ml of acetonitrile. To the mixture, 7.6 g (0.026 mol) of N-(γ-2,4-di-tert-amylphenoxy)propylamine was added under heating with stirring. After stirring for 2 hours, the mixture was cooled with water (10° to 20° C.). The crystals deposited were collected by filtration to obtain 11.5 g (77%) of Coupler (3). Melting Point: 155° to 157° C. (recrystallized from methanol).

Elemental Analysis for $C_{34}H_{47}NO_6S$:
Calcd. (%): C: 68.31, H: 7.93, N: 2.34.
Found (%): C: 68.41, H: 8.01, N: 2.38.

SYNTHESIS EXAMPLE 2

Synthesis of 1-Hydroxy-4-(β-methylsulfonylethoxy)-N-n-hexadecyl-2-naphthamide: Coupler (2)

10 g (0.023 mol) of 1,4-dihydroxy-N-n-hexadecyl-2-naphthamide, 5.7 g (0.046 mol) of methylsulfonylethanol and 4.4 g (0.023 mol) of p-toluenesulfonic acid were added to 50 ml of dehydrated toluene. The mixture was refluxed with heating for 5 hours and the water produced was removed. Toluene was removed under reduced pressure. 100 ml of methanol was added to the mixture. The crystals thus deposited were collected by filtration to obtain 10.8 g (88%) of Coupler (2). Melting Point: 107° to 109° C. (recrystallized from methanol).

Elemental Analysis for $C_{30}H_{47}NO_5S$:
Calcd. (%): C: 67.50, H: 8.87, N: 2.62.
Found (%): C: 67.24, H: 8.85, N: 2.51.

SYNTHESIS EXAMPLE 3

Synthesis of 1-Hydroxy-4-[β-(p-toluene)sulfonylethoxy]-N-[γ-(2,4-di-tert-amylphenoxy)propyl]-2-naphthamide: Coupler (6)

60 g (0.3 mol) of 1,4-dihydroxy-2-naphthoic acid was added to 150 ml of 2-bromomethanol and the mixture was reacted for 2 hours while bubbling hydrogen chloride gas under heating at 90° C. with stirring. After cooling (10° to 20° C.), the crystals thus deposited were collected by filtration to obtain 47.4 g (50%) of 1-hydroxy-4-(β-bromethoxy)-2-naphthoic acid.

31 g (0.1 mol) of the naphthoic acid derivative thus obtained and 42 g (0.2 mol) of sodium p-toluenesulfonic acid were dissolved into 300 ml of dimethylformamide and the solution was heated at 70° to 80° C. with stirring for 5 hours. After cooling, 1 liter of water was added to the mixture and the crystals thus deposited were collected by filtration to obtain 14.7 g (38%) of 1-hydroxy-4-[β-(p-toluene)sulfonylethoxy]-2-naphthoic acid.

7.7 g (0.02 mol) of 1-hydroxy-4-[β-(p-toluene)sulfonylethoxy]-2-naphthoic acid, 4.2 g (0.03 mol) of p-nitrophenol and 0.5 ml of dimethylformamide were added to 80 ml of acetonitrile. To the mixture, 4.7 g (0.04 mol) of thionyl chloride was added while refluxing by heating with stirring. After reacting for 1 hour, the crystals deposited were collected by filtration to obtain 10 g (98%) of p-nitrophenyl ester of 1-hydroxy-4-[β-(p-toluene)sulfonylethoxy]-2-naphthoic acid.

10 g (0.02 mol) of the p-nitrophenyl ester thus obtained was added to 100 ml of acetonitrile. To the mixture, 6.7 g (0.023 mol) of N-(γ-2,4-di-tert-amylphenoxy)propylamine was added while heating with stirring. After stirring for 2 hours, the mixture was cooled with water (10° to 20° C.) and the crystals thus deposited were collected by filtration to obtain 9.5 g (72%) of Coupler (6). Melting Point: 187° to 189° C. (recrystalized from acetonitrile).

Elemental Analysis for $C_{39}H_{49}NO_6S$:
Calcd. (%): C: 71.08, H: 7.49, N: 2.13.
Found (%): C: 70.93, H: 7.31, N: 2.08.

SYNTHESIS EXAMPLE 4

Synthesis of
1-Hydroxy-4-[β-(β'-hydroxyethyl)sulfonylethoxy]-N-n-hexadecyl-2-naphthamide: Coupler (7)

20 g (0.046 mol) of 1,4-dihydroxy-N-n-hexadecyl-2-naphthamide, 21 g (0.14 mol) of dihydroxyethylsulfone and 8.8 g (0.046 mol) of p-toluenesulfonic acid were added to 200 ml of dehydrated toluene. The mixture was refluxed with heating for 10 hours and water produced was removed. Toluene was removed under reduced pressure. 300 ml of methanol was added to the mixture and crystals thus deposited were collected by filtration and further the crystals deposited in the filtrate were collected to obtain 13.0 g (50%) of Coupler (7). Melting Point: 100° to 101° C. (recrystallized from ethanol).

Elemental Analysis for $C_{31}H_{49}NO_6S$:
Calcd. (%): C: 8.76, H: 66.04, N: 2.48.
Found (%): C: 8.77, H: 65.81, N: 2.22.

One or more of the couplers of this invention can be used to produce a silver halide color photographic light-sensitive material using the coupler of the present invention.

The following types of known couplers may also be incorporated in the photographic light-sensitive material which contains the couplers of the present invention. For example, the cyan dye forming couplers set forth in, for example, U.S. Pat. Nos. 2,474,293, 3,034,892, 3,592,383, 3,311,476, 3,476,563, etc., compounds which can release development inhibiting compounds during color development (referred to DIR couplers or DIR compounds) set forth, for example, in U.S. Pat. Nos. 3,632,345, 3,227,554, 3,378,529, etc., the yellow dye forming couplers disclosed, for example, in German Patent Application (OLS) No. 2,213,461, U.S. Pat. No. 3,510,306, etc., and the magenta dye forming couplers disclosed in, for example, U.S. Pat. No. 3,615,506, Japanese Patent Application No. 56050/1973, German Patent Application (OLS) No. 2,418,959, etc.

One or more of these couplers can be incorporated in the same layer of the photographic light-sensitive material, or a coupler may be present in two or more layers thereof, depending on the requirements of the characteristics thereof.

Suitable silver halide emulsions which can be used in the present invention include those containing silver chloride and silver bromide as well as mixed halides of silver such as silver chlorobromide, silver iodobromide, silver chloroiodobromide, etc.

The silver halide grains of these emulsions may be of a cubic form, an octahedral form, or may have a mixed crystalline structure.

The silver halide grain size distribution may be narrow or broad, and is not particularly limited. Suitable methods of preparing the silver halide emulsion which can be used include those well known in the art, such as the single and double jet process, the controlled double jet process, etc.

Two or more types of silver halide emulsions which have been prepared separately using different processes can be employed. The grain structure of the silver halide may be uniform or different from the surface to the interior, or may be of the so-called "conversion" type as described in British Pat. No. 635,841 and U.S. Pat. No. 3,622,318.

Further, silver halide grains which provide latent images primarily at the surface thereof or in the interior can be employed in the present invention.

The silver halide emulsions used in this invention may be chemically sensitized using well-known chemical sensitizers including N,N,N'-trimethylthiourea, the complex salts of monovalent gold such as the thiocyanates or the thiosulfates, etc., stannous chloride, hexamethylenetetramine, etc.

The layers of the photographic material can be coated using any known coating method including dip coating, air-knife coating, curtain coating, extrusion coating using a hopper as described in U.S. Pat. No. 2,681,294 and using a simultaneous multilayer coating as set forth in U.S. Pat. Nos. 2,761,791, 3,508,947, 2,941,898, 3,526,528, etc.

Suitable hydrophilic high molecular weight materials which can be present in the photographic coatings of the present invention include gelatin, cellulose derivatives, such as carboxymethylcellulose, hydroxyethylcellulose, etc., carbohydrate derivatives, such as starch derivatives, synthetic hydrophilic colloid materials, such as poly(vinyl alcohol), poly(N-vinylpyrrolidone), copolymers containing acrylic acid, polyacrylamide and the derivatives or partially hydrolyzed products of the above-described polymers, etc. Of these, the most representative is gelatin and gelatin is most generally used. The gelatin can be partly or completely replaced by a synthetic polymer or a gelatin derivative.

The photographic materials of the present invention may comprise photographic emulsions spectrally sensitized or supersensitized so as to be sensitive to blue, green or red light using cyanine dyes, such as cyanine, merocyanine, carbocyanine, etc., dyes, alone or as combinations thereof or in combination with styryl dyes. Descriptions of suitable spectral sensitization techniques appear in, for example, U.S. Pat. No. 2,493,748 for the blue region, U.S. Pat. No. 2,688,545 for the green region and U.S. Pat. No. 3,511,664 for the red region.

The photographic emulsion containing the coupler according to the present invention may contain a stabilizer or an antifoggant well-known in the art (e.g., 4-hydroxy-6-methyl-1,3,3a,7-tetrazaindene, 3-methylbenzothiazole, 1-phenyl-5-mercaptotetrazole, mercury compounds, mercapto compounds, certain metal salts, etc.).

A synthetic polymeric material can be mixed with the hydrophilic colloid such as gelatin in the photographic emulsion layer and other layers of the photographic color material of the present invention. A typical example of such a polymeric material is an aqueous latex of vinyl polymers as disclosed in U.S. Pat. No. 2,376,005, etc.

Various processes for dye image formation based on a number of different types of light-sensitive materials can be used in the present invention. First, the coupler-in-developer type color process is suitable in which the silver halide light-sensitive material is processed with a color developer solution which contains an aromatic primary amine color developing agent and a coupler dissolved whereby a water-insoluble or non-diffusible dye image results within the emulsion layer. For instance, couplers (17) and (23) illustrated hereinbefore can be used for such a process. Another process which can be used comprises processing a light-sensitive material containing a non-diffusible coupler in a silver halide emulsion layer with an alkaline developer solution containing an aromatic primary amine color developing agent to obtain a water-insoluble or non-diffusible dye image in the emulsion layer. For instance, couplers (1), (2), (6) and (11) described hereinbefore can be used for this type of process.

Couplers used in the present invention comprising phenol or α-naphthol derivatives are usually dispersed into the photographic emulsion in the form of a solution using aqueous or organic solvent systems. Of the couplers of the present invention, oil-soluble, non-diffusible couplers which are used for the incorporated coupler type process are generally incorporated into the photographic emulsion in the form of minute colloidal particles thereof after the couplers are dissolved in a suitable organic solvent. According to the present invention, the methods in which oil-soluble, non-diffusible couplers are dissolved in an organic solvent and incorporated into a photographic emulsion are preferred since the fullest effects of the present invention are achieved.

In oil-soluble, non-diffusible couplers of the couplers represented by the general formulae (IIA) or (IIB), one of the substituents represented by $R_1$ to $R_8$ is a group in which a ballast group containing a hydrophobic residue of 8 to 30 carbon atoms is bonded to the coupler skeleton directly or through an imino bond, an ether bond, a thioether bond, a carbonamido bond, a sulfonamido bond, a ureido bond, an ester bond, a carbonyl bond, an imido bond, a carbamoyl bond, a sulfamoyl bond, etc. Examples of suitable ballast groups are an alkyl group, an alkoxyalkyl group, an alkenyl group, an aryl group substituted with an alkyl group, an aryl group substituted with an alkoxy group, a terphenyl group and the like. These ballast groups can be substituted with one or more of a halogen atom such as fluorine, chlorine, etc., a nitro group, an amino group, a cyano group, an alkoxycarbonyl group, an aryloxycarbonyl group, an amido group, a carbamoyl group, a sulfamoyl group, a ureido group, a sulfonamido group and the like. Specific examples of suitable ballast groups are 2-ethylhexyl, tert-octyl, n-dodecyl, 2,2-dimethyldodecyl, n-octadecyl, 2-(n-hexyl)decyl, 9,10-dichlorooctadecyl, 2,4-di-tert-amylcyclohexyl, dodecyloxypropyl, oleyl, 2,4-di-tert-amylphenyl, 2,4-di-tert-amyl-6-chlorophenyl, 3-n-pentadecylphenyl, 2-dodecyloxyphenyl, 3-hexadecyloxyphenyl, o-terphenyl, perfluoroheptyl and the like.

Specific examples of the methods for dispersing non-diffusible couplers are described in greater detail in U.S. Pat. No. 3,676,131. Organic solvents, which are used to dissolve the coupler, which are insoluble or only sparingly soluble in water and having high boiling points remain in the photographic color material along with the coupler. Examples of these solvents include substituted hydrocarbons, carboxylic acid esters, carboxylic acid amides, phosphoric acid esters and ethers. Specific examples of such organic solvents include di-n-butyl phthalate, diisooctyl acetate, di-n-butyl sebacate, tricresyl phosphate, tri-n-hexyl phosphate, tri-cyclohexyl phosphate, N,N-diethylcaprylamide, butyl-n-pentadecyl phenyl ether, chlorinated paraffin, butyl benzoate, pentyl o-methylbenzoate, propyl 2,4-dichlorobenzoate, etc. In addition to these high boiling solvents, an auxiliary solvent which promotes coupler dissolution and which can be removed during the production of the light-sensitive material can be advantageously used. Examples of suitable solvents include propylene carbonate, ethyl acetate, butyl acetate, cyclohexanol, tetrahydrofuran, cyclohexanone, etc.

Surface active agents are advantageously used in order to disperse the oil-soluble coupler of the form of extremely fine particles into the hydrophilic polymeric matrix of the photographic emulsion. Specifically, anionic surfactants, such as sodium cetyl sulfate, sodium p-dodecylbenzenesulfonate, sodium nonylnaphthalene sulfonate, sodium di(2-ethylhexyl)-α-sulfosuccinate, etc., and nonionic surface active agents, such as sorbitan sesquioleate, sorbitan monolaurate, etc., can be used.

The dispersion of the oil-soluble couplers can be achieved using an emulsifying homogenizer, a colloid mill, an ultrasonic emulsifier, etc.

Examples of silver halide light-sensitive materials in which the coupler of the present invention can be used include color negative films, color positive films, color reversal films, color papers and other color photographic products for general use. Further, the couplers of the present invention can be used in color direct positive products, monochromatic products, color radiographic products, etc.

The couplers of the present invention can be used in multilayer color photographic materials of the conventional type (e.g., those described in U.S. Pat. Nos. 3,726,681, 3,516,831, British Pat. No. 923,045, etc.), in the processes set forth in Japanese Patent Application (OPI) No. 5179/1975, and also in the methods disclosed in German Patent Application (OLS) No. 2,322,165 and U.S. Pat. No. 3,703,375 in which they are used in combination with a DIR compound.

The amount of the coupler of the present invention is not restricted. A preferred amount of the coupler of this invention when incorporated into a photographic material, which can be varied depending on the requirements, generally ranges between about 1 and about 1,500 g per mol of silver halide.

Silver halide photographic materials of the present invention comprise a support and various coatings thereon, such as a silver halide emulsion layer, an intermediate layer, an antihalation layer, a protective layer, a yellow filter layer, a backing layer, a mordanting polymer layer, a layer for preventing stains by the developer, etc. The silver halide emulsion layers for color photography comprise a red sensitive silver halide emulsion layer, a green sensitive silver halide emulsion layer and a blue sensitive silver halide emulsion layer. There is no particular limitation on the layer arrangement thereof, and further each of these layers may be divided into two or more layers.

When a p-substituted phenol derivative is present in the silver halide emulsion layer or in a layer adjacent thereto of the light-sensitive material used in the present invention, the stability of the finished color photographs is advantageously enhanced. Particularly effective p-substituted phenol derivatives which can be used include the hydroquinone derivatives disclosed in U.S. Pat. Nos. 2,360,290, 2,418,613, 2,675,314, 2,701,197, 2,704,713, 2,710,801, 2,728,659, 2,732,300, 2,735,765 and 2,816,028, the gallic acid derivatives set forth in U.S. Pat. Nos. 3,457,079 and 3,069,262, Japanese Patent Publication No. 13496/1968, the p-alkoxyphenol derivatives disclosed in U.S. Pat. Nos. 2,735,765 and Japanese Patent Application (OPI) No. 4738/1972, the p-oxyphenol derivatives described in U.S. Pat. Nos. 3,432,300, 3,573,050, 3,574,627 and 3,764,337.

An ultraviolet absorbing agent may be advantageously employed in order to improve the fastness of the dye images formed. The ultraviolet absorbing agent can be present either in the silver halide emulsion layer itself or in layers adjacent thereto. Those ultraviolet absorbing agents described in, for example, U.S. Pat. Nos. 3,250,617, 3,253,921, etc., can be used.

The silver halide emulsion and other layers can be hardened using any conventionally known methods employing aldehyde compounds, such as formaldehyde, glutaraldehdye, etc., ketone compounds, such as diacetyl or cyclopentanedione, compounds having a reactive halogen, such as bis(2-chloroethylurea), 2-hydroxy-4,6-dichloro-1,3,5-triazine, and those described in U.S. Pat. Nos. 3,288,775, 2,732,303, 3,125,449 and 1,167,207, compounds having a reactive olefinic group, such as divinyl sulfone, 5-acetyl-1,3-diacryloyl-hexahydro-1,3,5-triazine, and those set forth in U.S. Pat. Nos. 3,635,718 and 3,232,763, British Pat. No. 994,869, etc., N-methylol compounds such as N-hydroxymethyl phthalimide and those set forth in U.S. Pat. Nos. 2,732,316 and 2,586,168, etc., isocyanate compounds disclosed in U.S. Pat. No. 3,103,437, aziridine compounds set forth in U.S. Pat. Nos. 3,017,280 and 2,983,611, etc., acid derivatives described in U.S. Pat. Nos. 2,725,294 and 2,725,295, etc., carbodiimide derivatives such as those described in U.S. Pat. No. 3,100,702, etc., epoxy compounds set forth in, for example, U.S. Pat. No. 3,091,537, isoxazoles disclosed in U.S. Pat. Nos. 3,321,313 and 3,543,292, halocarboxyaldehyde compounds including mucochloric acid, dioxane derivatives such as dihydroxydioxane, dichlorodioxane, etc., or inorganic hardening agents such as chrome alum, zirconium sulfate, etc.

Precursors of hardening agents can also be used with examples of such precursors including alkali metal bisulfite/aldehyde adducts, the methylol derivative of hydantoin, primary aliphatic nitro alcohols, etc.

The color photographic material of the present invention can be subjected to conventional and well known processings comprising, after exposure, color development, bleaching and fixing. Each processing step may be combined with another using a processing agent capable of accomplishing the corresponding functions. A typical example of such a combined processing is a mono-bath process using a blix solution.

Depending on the requirements, the development processing can include additional steps such as pre-hardening, neutralization, primary development (black-and-white development), image stabilization, washing with water, etc. The processing temperature, which is determined depending on the kind of photographic material as well as by the processing composition, is sometimes below about 18° C., but, in most cases, is not lower than 18° C.

A particularly useful temperature range is from about 20° to 60° C. The temperature may be varied from one processing step to another in the processing.

A color developer comprises an aqueous alkaline solution with a pH not lower than about 8, and more preferably between 9 and 12, containing a color developing agent the oxidation product of which is capable of reacting with a coupler to form a dye.

Suitable color developing agents which can be used include, for example, 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 4-amino-3-methyl-N-ethyl-N-$\beta$-methanesulfamidoethylaniline, 4-amino-N,N-dimethylaniline, 4-amino-3-methoxy-N,N-diethylaniline, 4-amino-3-methyl-N-ethyl-N-$\beta$-methoxyethylaniline, 4-amino-3-methoxy-N-ethyl-N-$\beta$-methoxyethylaniline, 4-amino-3-$\beta$-methanesulfamidoethyl-N,N-diethylaniline, and the salts thereof, such as the sulfates, the hydrochlorides, the sulfites, the p-toluenesulfonates, etc. Other color developing agents which can be used are described in U.S. Pat. Nos. 2,592,364 and 2,193,015, Japanese Patent Application (OPI) No. 64933/1973, L.F.A. Mason, *Photographic Processing Chemistry*, pp. 226–229, Focal Press, London (1966), etc.

Each of the above-described compounds can be used in conjunction with 3-pyrazolidone derivatives. Further, a number of additives well-known in the art may be present in the color developer.

The coupler of this invention can also be incorporated into the color developer and a suitable amount of the coupler of this invention which can be used in the color developing solution is about 0.5 to 20 g per liter of the developing solution.

The photographic material of the present invention is subjected to bleaching after color development. This step may be combined with fixing, whereby the processing solution contains a fixing agent in addition to a bleaching agent.

Suitable bleaching agents include ferricyanide salts, bichromate salts, water-soluble cobalt(III) salts, water-soluble copper(II) salts, water-soluble quinones, nitrosophenol, polyvalent metal compounds containing Fe(III), Co(III), Cu(II), with complex salts of such metals with organic acids, such as, for example, ethylenediamine tetraacetic acid, nitrilotriacetic acid, imidoacetic acid, N-hydroxyethylethylenediamine triacetic acid and other aminopolycarboxylic acid, malonic acid, tartaric acid, malic acid, diglycolic acid, dithioglycolic acid and 2,6-dipicolic acid copper complex salt, etc., being particularly preferred, peracids, such as alkyl peracids, persulfates, permanganates, hydrogen peroxide, etc.; hypochlorites, etc.

Other additives, such as bleach accelerating agents as disclosed in U.S. Pat. Nos. 3,042,520 and 3,241,966, Japanese Patent Publication Nos. 8506/1970 and 8836/1970, etc., can be further added to the bleaching solution.

It has been found that the couplers in accordance with the present invention can be used even for light-sensitive materials of the low silver content type in which the amount of silver halide in the emulsion is from several to one hundred times smaller than that of the ordinary type. Using such a color light-sensitive material of the low silver content type, color images of sufficiently high density can be obtained using the color intensification process in which a peroxide or a cobalt complex salt is employed (for example, as disclosed in German Patent Application (OLS) No. 2,357,694, U.S. Pat. Nos. 3,674,490 and 3,761,265, German Patent Application (OLS) Nos. 2,044,833, 2,056,359, 2,056,360 and 2,226,770, Japanese Patent Application (OPI) Nos. 9728/1973 and 9729/1973, etc.).

The present invention is further described more specifically by reference to the following examples thereof, but the present invention is not to be construed as being limited to these examples.

EXAMPLE 1

To 10 g of Coupler (2), i.e., 1-hydroxy-4-(β-methylsulfonylethoxy)-N-n-hexadecyl-2-naphthamide, were added 10 ml of di-n-butyl phthalate and 20 ml of ethyl acetate. The mixture was heated at 50° C. to prepare a solution. The resulting solution was added to 100 ml of an aqueous solution containing 10 g of gelatin and 0.5 g of sodium p-dodecylbenzenesulfonate, and the mixture was mechanically agitated vigorously using a high speed agitator for 20 minutes whereby the coupler was dispersed in time droplets together with the solvent.

60.1 g of this dispersion was added to 100 g of a photographic emulsion comprising 0.03 mol of silver chloroiodide (bromide content: 50 mol%) and 8 g of gelatin. After the addition of 12 ml of a 2% aqueous solution of the sodium salt of 2-hydroxy-4,6-dichloro-s-triazine as a hardener and adjustment to a pH of 6.5, the emulsion was coated on a cellulose triacetate film in a silver coating rate of $8.5 \times 10^{-3}$ mol/m$^2$. The photographic material thus-prepared was designated Sample A. The content of the coupler was $2.15 \times 10^{-3}$ mol/m$^2$ in Sample A.

The same processes were repeated to prepare photographic light-sensitive materials except that in place of Coupler (2), 10 g of 1-hydroxy-4-chloro-N-n-hexadecyl-2-naphthamide [Coupler a] and 10 g of 1-hydroxy-4-tetradecyloxy-N-n-hexadecyl-2-naphthamide [Coupler b] was employed and 50.5 g and 70.3 g of the dispersion was added, respectively. These samples were designated Sample B and Sample C, respectively. The content of the coupler in Sample B and Sample C was $2.15 \times 10^{-3}$ mol/m$^2$ and $2.13 \times 10^{-3}$ mol/m$^2$, respectively.

After sensitometric exposure to a step wedge, each photographic light-sensitive material was subjected to the following processings in the order listed.

| Processing Step | Temperature (°C.) | Time (min) |
|---|---|---|
| 1. Color Development | 24 | 8 |
| 2. Washing with Water | " | 1 |
| 3. First Fixing | " | 4 |
| 4. Washing with Water | " | 3 |
| 5. Bleaching | " | 6 |
| 6. Washing with Water | " | 3 |
| 7. Second Fixing | " | 4 |
| 8. Washing with Water | " | 10 |

The color developer solution used had the following composition.

| Color Developer Solution | |
|---|---|
| Sodium Sulfite (anhydrous) | 3.0 g |
| 4-Amino-3-methyl-N,N-diethylaniline Hydrochloride | 2.5 g |
| Sodium Carbonate (monohydrate) | 47.0 g |
| Potassium Bromide | 2.0 g |
| Water to make | 1,000 ml |

The fixing solution and the bleaching solution used had the following compositions.

| First and Second Fixing Solution | |
|---|---|
| Sodium Thiosulfate | 150 g |
| Sodium Sulfite | 15 g |
| Glacial Acetic Acid (28% aq. soln.) | 48 ml |
| Boric Acid | 7.5 g |
| Water to make | 1,000 ml |
| Bleaching Solution | |
| Potassium Bromide | 20 g |
| Potassium Ferricyanide | 100 g |
| Glacial Acetic Acid | 20 ml |
| Sodium Acetate | 40 g |
| Water to make | 1,000 ml |

After the processing the optical density to red light of Samples A, B and C was measured, and the results obtained are shown in Table 1 below.

TABLE 1

| Film Sample | Coupler | Coupler Coating Rate | Fog | Relative* Sensitivity | Gamma | Maximum Density |
|---|---|---|---|---|---|---|
| A | (2) | $2.15 \times 10^{-3}$ | 0.05 | 100 | 3.35 | 3.52 |
| B | (a) | $2.15 \times 10^{-3}$ | 0.05 | 91 | 2.23 | 3.20 |
| C | (b) | $2.13 \times 10^{-3}$ | 0.04 | 72 | 1.65 | 2.17 |

*The relative value of reciprocal amount of exposure required to obtain a density of fog + 0.1.

Next, the time of the processing for the color development was changed for Samples A, B and C to determine the dependence of the maximum density for red light on the development time. The results obtained are given in Table 2 below.

TABLE 2

| Film Sample | Coupler | Developing Time (minutes) | | |
|---|---|---|---|---|
| | | 4 | 8 | 15 |
| A | (2) Present Invention | 3.40 | 3.52 | 3.54 |
| B | (a) Comparison | 3.00 | 3.20 | 3.33 |
| C | (b) Comparison | 1.94 | 2.17 | 2.35 |

The results obtained above clearly demonstrate that the coupler used in the present invention in which the active site is substituted with a β-methylsulfonylethoxy group results in a higher sensitivity, a higher gradation and a higher color density in comparison with a coupler used in the comparison samples such as Coupler (a) in which the active site is substituted with a chlorine atom, or Coupler (b) in which the active site is substituted with a tetradecyloxy group, and that such a large density can be developed in a short processing time, enabling a reduction in the processing period of time.

When Coupler (7) was used in place of Coupler (2) with the same processing, similarly advantageous results were obtained for sensitivity, gradation and color density, showing the superiority of the coupler of this invention to a coupler in which the active site is substituted with a chlorine atom or a coupler in which the active site is substituted with a tetradecyloxy group.

In order to confirm this improved coupling reactivity the following experiment was carried out.

Couplers (2) and (7) of the present invention and Coupler (a) and (b) each was admixed with a yellow color forming Coupler (c), i.e., α-(4-methoxybenzoyl)-2-chloro-5-[α-(2,4-di-tert-amylphenoxy)-butyramido]acetanilide in a molar ratio of 1:2. The sample prepared in the same procedure as Sample A using the mixture of couplers was color developed using 4-amino-3-methyl-N,N-diethylaniline as a color developing agent. The analysis of the ratio of the formed cyan dye to the yellow dye, from which the relative value (based on the yellow color forming Coupler (c)) of the reaction rate constant in the coupling reaction of the cyan coupler of the present invention was calculated. The relative value of the reaction rate constant was determined by measuring the amounts of dyes in the color images obtained by mixing two couplers M and N which give clearly separate and distinct colors and adding the mixture to an emulsion, and then performing color development. If coupler M develops color of the maximum density $(D_M)_{max}$ and color of density $D_M$ in an intermediate stage, and coupler N develops colors of $(D_N)_{max}$ and $D_N$ respectively, the ratio $R_M/R_N$ of the reaction activities of both couplers is expressed by the following equation.

$$\frac{R_M}{R_N} = \frac{\log(1 - \frac{D_M}{(D_M)_{max}})}{\log(1 - \frac{D_N}{(D_N)_{max}})}$$

In other words, the coupling activity ratio $R_M/R_N$ can be obtained from the gradient of the straight line which is obtained by plotting several sets of $D_M$ and $D_N$ resulting from imparting several stages of exposure to an emulsion containing a mixed coupler and subjecting them to color development, on two axes crossing at right angles to each other as $\log(1 - D/D_{max})$.

Coupler (2) and Coupler (7) in which the active site is substituted with a sulfonylethoxy group according to the present invention gave a relative rate constant of 1.7 and 1.8, respectively, while the known Coupler (a) in which the active site is substituted with a chlorine atom and the known Coupler (b) in which the active site is substituted with a tetradecyloxy group gave 1.2 and 0.8, respectively. These results illustrate that the couplers of the present invention are excellent couplers in that their reactivity is improved.

EXAMPLE 2

To 10 g of Coupler (1), i.e., 1-hydroxy-4-(β-methylsulfonylethoxy)-N-[γ-(2,4-di-tert-amylphenoxy)-propyl]-2-naphthamide were added 10 ml of tricresyl phosphate, 20 ml of ethyl acetate and 0.5 g of sodium di(2-ethylhexyl)-α-sulfosuccinate. The mixture was heated to 50° C. to promote the dissolution, then the mixture was added to 100 ml of an aqueous solution containing 10 g of gelatin. Dispersion was carried out using a homogenizer. The resultant product was designated Dispersion (A).

To 100 g of a silver iodobromide emulsion (iodide content: 7 mol%; silver content: $3.5 \times 10^{-2}$ mol; content of gelatin: 6 g) were added 42.0 g of Dispersion (A), then 5 ml of a 2% methanol solution of 5-methyl-7-hydroxy-1,3,4,7a-tetrazaindene and 6.5 ml of a 2% aqueous solution of sodium 2-hydroxy-4,6-dichloro-s-triazine as hardening agent. Finally, after the adjustment of the pH to 6.5, the mixture was coated on a cellulose triacetate film in a coupler coating rate of $2.05 \times 10^{-3}$ mol/m². This film was designated Sample D.

For the purposes of comparison, Coupler (e) which has the same coupler structure as Coupler (1) but with the active site unsubstituted, Coupler (f) in which the active site is substituted with an ethoxy group, Coupler (h) in which the active site is substituted with a butylcarbamyl methoxy group, Coupler (j) in which the active site is substituted with an ethoxycarbonylmethoxy group, and Coupler (k), i.e., 1-hydroxy-4-dodecyloxy-N-[γ-(2,4-di-tert-amylphenoxy)propyl]-2-naphthamide were used to prepare Dispersions (E), (F), (G), (H), (J) and (K) using the same procedures employed for Dispersion (A), respectively.

Using 200 g of the emulsion described above and 32.4 g of Dispersion (E), 100 g of the emulsion and 34.7 g of Dispersion (F), 100 g of the emulsion and 35.0 g of Dispersion (G), 100 g of the emulsion and 41.3 g of the Dispersion (H), 100 g of the emulsion and 39.4 g of Dispersion (J) and 100 g of the emulsion and 44.8 g of Dispersion (K), Samples E, F, G, H, J and K were prepared.

The contents of the couplers in these six samples were $2.08 \times 10^{-3}$ mol/m², $2.07 \times 10^{-3}$ mol/m², $2.05 \times 10^{-3}$ mol/m², $2.07 \times 10^{-3}$ mol/m², $2.07 \times 10^{-3}$ mol/m² and $2.05 \times 10^{-3}$ mol/m², respectively.

After sensitometric step wedge exposure, each of these seven samples was subjected to the following processings.

| Processing Step | Temperature (°C.) | Time (min) |
|---|---|---|
| 1. Color Development | 38 | 3 |
| 2. Stopping | " | 1 |
| 3. Washing with Water | " | 1 |
| 4. Bleaching | " | 2 |
| 5. Washing with Water | " | 1 |
| 6. Fixing | " | 2 |
| 7. Washing with Water | " | 1 |
| 8. Stabilizing Bath | " | 1 |

The processing solutions used had the following compositions.

| Color Developer Solution | |
|---|---|
| Sodium Hydroxide | 2 g |
| Sodium Sulfite | 2 g |
| Potassium Bromide | 0.4 g |
| Sodium Chloride | 1 g |
| Borax | 4 g |
| Hydroxylamine Sulfate | 2 g |
| Disodium Ethylenediamine Tetraacetate (dihydrate) | 2 g |
| 4-Amino-3-methyl-N-ethyl-N-(β-hydroxyethyl)aniline Monosulfate | 4 g |

| | |
|---|---|
| Water to make | 1,000 ml |
| Stopping Solution | |
| Sodium Thiosulfate | 10 g |
| Ammonium Thiosulfate (70% aq. soln.) | 30 ml |
| Acetic Acid | 30 ml |
| Sodium Acetate | 5 g |
| Potassium Alum | 15 g |
| Water to make | 1,000 ml |
| Bleaching Solution | |
| Fe(III) . Sodium Ethylenediamine Tetraacetate (dihydrate) | 100 g |
| Potassium Bromide | 50 g |
| Ammonium Nitrate | 50 g |
| Boric Acid | 5 g |
| Aqueous Ammonia | to adjust pH to 5.0 |
| Water to make | 1,000 ml |
| Fixing Solution | |
| Sodium Thiopsulfate | 150 g |
| Sodium Sulfite | 15 g |
| Borax | 12 g |
| Glacial Acetic Acid | 15 ml |
| Potassium Alum | 20 g |
| Water to make | 1,000 ml |
| Stabilizing Bath | |
| Boric Aid | 5 g |
| Sodium Citrate | 5 g |
| Sodium Metaborate (tetrahydrate) | 3 g |
| Potassium Alum | 15 g |
| Water to make | 1,000 ml |

After processing, the optical density to red light of each of these samples, i.e., D, E, F, G, H, J and K was measured and the results obtained are shown in Table 3 below.

TABLE 3

| Film Sample | Coupler | Coupler Coating Rate | Fog | Relative* Sensitivity | Gamma | Maximum Density |
|---|---|---|---|---|---|---|
| D | (1) | $2.05 \times 10^{-3}$ | 0.07 | 100 | 2.65 | 2.90 |
| E | (e) | $2.08 \times 10^{-3}$ | 0.06 | 70 | 1.67 | 2.23 |
| F | (f) | $2.07 \times 10^{-3}$ | 0.06 | 72 | 1.72 | 2.25 |
| G | (g) | $2.05 \times 10^{-3}$ | 0.07 | 77 | 1.85 | 2.00 |
| H | (h) | $2.07 \times 10^{-3}$ | 0.06 | 72 | 1.83 | 2.35 |
| J | (j) | $2.07 \times 10^{-3}$ | 0.07 | 85 | 2.08 | 2.60 |
| K | (k) | $2.05 \times 10^{-3}$ | 0.05 | 60 | 1.37 | 1.91 |

*The relative value of reciprocal amount of exposure required to obtain a density of fog + 0.10.

These results demonstrate that the coupler of the present invention containing the $\beta$-methylsulfonylethoxy group as the substituent at the active site can impart a higher sensitivity, a higher gradation and a higher maximum density to the photographic material containing the same in comparison to the corresponding couplers, Coupler (e) with an unsubstituted active site, Coupler (f) having a chlorine substituted active site, Coupler (g) having an ethoxy substituted active site, Coupler (h) having a butylcarbamylmethoxy substituted active site, Coupler (j) having an ethoxycarbonylmethoxy substituted active site, and Coupler (k) having a tetradecyloxy substituted active site used in each of the comparison samples. In addition, no deterioration in granularity of the resulting color image, which tends to result from strengthened coupling activity, was observed on examination under a microscope.

EXAMPLE 3

42.0 g of Coupler (6), i.e., 1-hydroxy-4-[$\beta$-(p-toluene)sulfonylethoxy]-N-[$\gamma$-(2,4-di-tert-amylphenoxy)propyl]-2-naphthamide was mixed with 40 ml of di-n-butylphthalate, 80 ml of ethyl acetate, and 2.0 g of sodium di(2-ethylhexyl)-$\alpha$-sulfosuccinate. A solution was obtained by heating the above mixture to 50° C. and the mixture was added to 400 ml of an aqueous solution containing 40 g of gelatin. On agitation, a turbid mixture resulted, which was further emulsified using a homogenizer.

A photographic emulsion was prepared by adding to 1.0 kg of a silver chlorobromide emulsion containing 0.3 mol silver and 70 g of gelatin (bromide content: 50 mol%), 200 ml of a 0.01% methanol solution of a red-sensitive spectral sensitizer designated Compound I-6 in Japanese Patent Publication No. 22189/1970 and then 50 ml of a 1% methanol solution of 5-methyl-7-hydroxy-1,3,4,7a-tetrazaindene.

The entire weight of the dispersion described above was added to all of this emulsion and, further, 30 ml of a 3% acetone solution of triethylenephosphamide was added as hardening agent. Finally, the pH was adjusted to 6.5 to prepare a red-sensitive silver halide emulsion.

On a substrate comprising baryta paper, both surfaces of which had been treated with polyethylene, a first layer comprising a blue-sensitive silver halide emulsion containing Coupler (m), i.e., $\alpha$-(5,5-dimethyl-2,4-dioxooxazolidin-3-yl)-$\alpha$-pivaloyl-2-chloro-5-[$\alpha$-(2',4'-di-tert-amylphenoxy)butyramido]acetanilide was coated in a dry thickness of 4.0 microns. Then, a gelatin solution was coated thereon in a dry thickness of 1.0 micron as a second layer, and a third layer comprising a green-sensitive silver halide emulsion containing Coupler (n), i.e., 1-(2,4,6-trichlorophenyl)-3-[(2-chloro-5-n-tetradecanamido)anilino]-5-pyrazolone was overcoated in a dry thickness of 2.5 microns. A fourth layer was provided by coating a gelatin solution containing 2-(2'-benzotriazolyl)-4,6-dibutylphenol as an ultraviolet absorbing agent in a dry thickness of 2.5 microns.

The red-sensitive silver halide emulsion described above was then coated in a thickness of 3.5 microns on dry basis as a fifth layer. As the outermost layer, a gelatin solution was coated in a dry thickness of 0.5 micron, whereby a color printing paper was prepared.

The color print paper thus-prepared was optically printed from a color negative original followed by the processing as described below.

| Processing Step | Temperature (°C.) | Time (min) |
|---|---|---|
| 1. Color Development | 30 | 6 |
| 2. Stopping | " | 2 |
| 3. Washing with Water | " | 2 |
| 4. Bleach-Fixing | " | 2 |
| 5. Washing with Water | " | 2 |
| 6. Stabilizing Bath | " | 2 |

The processing solutions used had the following compositions.

| Color Developer Solution | |
|---|---|
| Benzyl Alcohol | 12 ml |
| Diethylene Glycol | 3.5 ml |
| Sodium Hydroxide | 2.0 g |
| Sodium Sulfite | 2.0 g |
| Potassium Bromide | 0.4 g |
| Sodium Chloride | 1.0 g |
| Borax | 4.0 g |
| Hydroxamine Sulfate | 2.0 g |
| Disodium Ethylenediamine Tetraacetate (dihydrate) | 2.0 g |

-continued

| | |
|---|---|
| 4-Amino-3-methyl-N-ethyl-N-(β-methane-sulfonamidoethyl)aniline Sesquisulfate (monohydrate) | 5.0 ml |
| Water to make | 1,000 ml |
| Stopping Solution | |
| Sodium Thiosulfate | 10 g |
| Ammonium Thiosulfate (70% aq. soln.) | 30 ml |
| Sodium Acetate | 5 g |
| Acetic Acid | 30 ml |
| Potassium Alum | 15 g |
| Water to make | 1,000 ml |
| Bleach-Fixing Solution | |
| Ferric Sulfate | 20 g |
| Disodium Ethylenediamine Tetraacetate (dihydrate) | 36 g |
| Sodium Carbonate (monohydrate) | 17 g |
| Sodium Sulfite | 5 g |
| Ammonium Thiosulfate (70% aq. soln.) | 100 ml |
| Boric Acid | 5 g |
| pH adjusted to | 6.8 |
| Water to make | 1,000 ml |
| Stabilizing Bath | |
| Boric Acid | 5 g |
| Sodium Citrate | 5 g |
| Sodium Metaborate (tetrahydrate) | 3 g |
| Potassium Alum | 15 g |
| Water to make | 1,000 ml |

The resulting color print had an excellent appearance with brilliant colors, exhibiting a superior color reproduction capability. The cyan dye image had an absorption maximum at 710 millimicrons.

The light fastness of the image was examined by irradiating the color print with white fluorescent light at an intensity of 30,000 lux for 20 days. The density change of the cyan dye was 0.03 at the area with an initial reflection density of 1.0. Further, the stability of the image was excellent since storage under a high temperature and high humidity condition of 60° C. and 75% RH for 10 days decreased the cyan density only by 0.08 from the initial value of 1.0.

When a piece of the coated unexposed sample was left at 40° C. and 80% RH for 3 days and another piece at 25° C. and 60% RH for the same period, and then both pieces were subjected to sensitometric step wedge exposure, followed by the processing described above, no significant differences in maximum density, fog and gamma were observed, confirming that the photographic materials of the present invention possess satisfactory stability.

EXAMPLE 4

10 g of Coupler (12), i.e., N-n-hexadecyl-N-cyanoethyl-1-hydroxy-4-(β-phenylsulfonylethoxy)-2-naphthamide, was dissolved in 10 ml of tris-n-hexyl phosphate and 20 ml of ethyl acetate by heating to 50° C. The resulting solution was added to 100 ml of an aqueous solution containing 0.5 g of sodium p-dodecylbenzenesulfonate and 10 g of gelatin, and the mixture was mechanically stirred vigorously to disperse the couplers together with the solvent.

To 186 g of a reversal type silver iodobromide emulsion (iodide content: 3 mol%; Ag content: $8.37 \times 10^{-2}$ mol; gelatin content: 13.0 g) were added all of the dispersion thus-prepared and then 12 ml of a 4% aqueous solution of sodium 2-hydroxy-4,6-dichloro-s-triazone as a hardener. After adjustment of the pH to 7.0, the mixture was coated on a polyethylene terephthalate film in an Ag coating rate of 0.90 g/m².

After sensitometric exposure to step wedge, the following processings were carried out.

| Processing Step | Temperature (°C.) | Time (min) |
|---|---|---|
| 1. First Development | 30 | 3 |
| 2. Washing with Water | " | 0.5 |
| 3. Exposure for Image Reversal | intensity of 8,000 lux, 1 second | |
| 4. Second Development | 30 | 4 |
| 5. Washing with Water | " | 1 |
| 6. Bleaching | " | 1 |
| 7. Washing with Water | " | 0.5 |
| 8. Fixing | " | 1 |
| 9. Washing with Water | " | 1 |

The processing solutions used had the following compositions.

| First Developer Solution | |
|---|---|
| 4-(N-Methylamino)phenol Sulfate | 2 g |
| Sodium Sulfite | 90 g |
| Hydroquinone | 8 g |
| Sodium Carbonate (monohydrate) | 52.5 g |
| Potassium Bromide | 5 g |
| Potassium Thiocyanate | 1 g |
| Water to make | 1,000 ml |

The reversal color image thus-produced had an absorption maximum at 687 millimicrons exhibiting a superior color formation.

When another piece of the same sample was sensitometrically exposed to step wedge after storage for 3 days at 40° C., 75% RH, followed by the same processing as described above, an equivalent photographic performance as to maximum density, fog, gamma, sensitivity, etc., was obtained, confirming that the coupler used was satisfactorily stable.

EXAMPLE 5

A silver iodobromide emulsion containing 4 mol% iodide was coated on a film at a silver coating rate of 120 μg/cm² and in a thickness of 4.0 microns. This film was sensitometrically exposed to a step wedge, and processed with the following color developer solution at 27° C., for 4 minutes, followed by washing, bleaching, washing, fixing and washing in a manner similar to Example 1. A cyan dye image was obtained.

| Color Developer Solution | |
|---|---|
| Sodium Sulfite | 5 g |
| 4-Amino-3-methyl-N,N-diethylaniline Hydrochloride | 0.6 g |
| Sodium Carbonate (monohydrate) | 15 g |
| Potassium Bromide | 0.5 g |
| Potassium Iodide (0.1% aq. soln.) | 5 ml |
| 2-Acetamido-6-chloro-4-(β-methyl-sulfonylpropyl)-5-methylphenol (Coupler (23)) | 1.3 g |
| Methanol | 20 ml |
| Sodium Hydroxide | 20 ml |
| Water to make | 1,000 ml |

The brilliant cyan color image having an absorption maximum at 672 millimicrons was obtained.

While the invention has been described in detail and with reference to specific embodiments thereof, it will be apparent to one skilled in the art that various changes and modifications can be made therein without departing from the spirit and scope thereof.

What is claimed is:

1. A photographic silver halide light-sensitive material comprising a support having thereon at least one silver halide emulsion layer containing a cyan dye-forming colorless photographic coupler wherein the coupling position capable of reacting with the oxidized product of an aromatic primary amine developing agent is substituted with at least one alkoxy group substituted with a sulfonyl group as a coupling-off group, said alkoxy group being represented by the formula (I):

$$-O-R-SO_2-R_1 \qquad (I)$$

wherein R represents a saturated or unsaturated divalent aliphatic group having 1 to 4 carbon atoms which may be straight or branched chain and may be substituted provided that R is not substituted with an aryl group at the α-position; and $R_1$ represents an aliphatic group, an aromatic group.

2. A photographic silver halide light-sensitive material comprising a support having thereon at least one silver halide emulsion layer containing a cyan dye-forming colorless photographic coupler represented by the general formulae (Ia) or (Ib):

$$A(O-R-SO_2-R_1)_n \qquad (Ia)$$

$$A-O-R-SO_2-R'-O-A' \qquad (Ib)$$

wherein A represents a phenolic or naphtholic group; A' represents a phenolic or naphtholic group which may be the same as or different than A; R and R', which may be the same or different, each represents a saturated or unsaturated divalent aliphatic group; $R_1$ represents an alkyl group, an alkenyl group, an aralkyl group, r an aralkenyl group, or an aryl group; and n represents a positive integer.

3. The photographic material of claim 2, wherein the alkyl group, the alkenyl group, the aralkyl group, the aralkenyl group and, the aryl group represented by $R_1$ may be unsubstituted or substituted with one or more of a halogen atom, a nitro group, a cyano group, a hydroxy group, an alkoxy group, an acyloxy group, an acylamino group, a sulfonamido group, a sulfamoyl group, a sulfonyl group, a carboxy group or a sulfo group.

4. The photographic material of claim 2, wherein the sulfonyl group of the alkoxy group is positioned at the α-, β- or γ-position of the alkoxy group.

5. The photographic material of claim 1, wherein the coupler is represented by the general formulae (IIA) or (IIB):

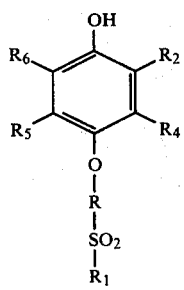

(IIA)

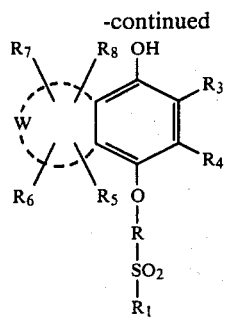

(IIB)

wherein R and $R_1$ each has the same meaning as defined in the formula (I); $R_2$ represents a hydrogen atom, an aliphatic group containing up to 30 carbon atoms, an alkoxy group containing up to 30 carbon atoms, an aryloxy group, an acylamido group, a sulfonamido group, a phosphoramido group, a ureido group, or a carbamyl group, each represented by the general formulae (III) to (VIII):

$$-NH-CO-B \qquad (III)$$

$$-NH-SO_2-B \qquad (IV)$$

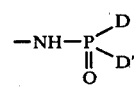 (V)

$$-NHCONH-B \qquad (VI)$$

$$-CONH-B \qquad (VII)$$

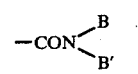 (VIII)

wherein B and B', which may be the same or different, each represents an aliphatic group containing 1 to 32 carbon atoms, or an aryl group, wherein the alkyl group and the aryl group may be substituted with one or more of a halogen atom, a nitro group, a cyano group, a hydroxy group, a carboxy group, an amino group, an alkyl group, an aryl group, an alkoxycarbonyl group, an acyloxycarbonyl group, an amido group, an imido group, a carbamoyl group, a sulfamoyl group, an alkoxy group, or an aryloxy group; and D and D', which may be the same or different, each represents the groups described for B and additionally an —OB group, an —NH—B group, or an —NB_2 group; $R_3$ represents a hydrogen atom, an aliphatic group containing up to 30 carbon atoms, or a carbamoyl group represented by said formulae (VII) or (VIII); $R_4$, $R_5$, $R_6$, $R_7$ and $R_8$, which may be the same or different, each represents a hydrogen atom, a halogen atom, an alkyl group, an aryl group, an alkoxy group, an alkylthio group, a heterocyclic ring, an amino group, a carbonamido group, a sulfonamido group, a sulfamoyl group or a carbamoyl group; and W represents a non-metallic atomic group necessary to complete a 5- or 6-membered ring.

6. The photographic material of claim 5, wherein the coupler is represented by the general formula (IIA):

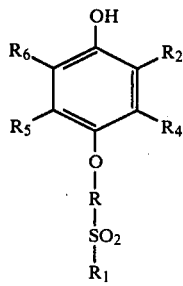

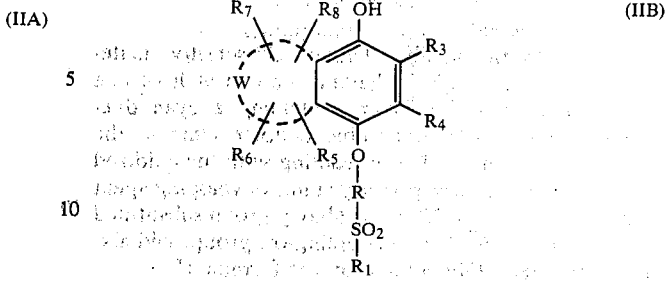

wherein R and R₁ each has the same meaning as defined in the formula (I); R₂ represents a hydrogen atom, an aliphatic group containing up to 30 carbon atoms, an alkoxy group containing up to 30 carbon atoms, an aryloxy group, an acylamido group, a sulfonamido group, a phosphoramido group, a ureido group, or a carbamyl group, each represented by the general formulae (III) to (VIII):

$$-NH-CO-B \quad (III)$$

$$-NH-SO_2-B \quad (IV)$$

$$-NH-\underset{\underset{O}{\|}}{P}\overset{D}{\underset{D'}{}} \quad (V)$$

$$-NHCONH-B \quad (VI)$$

$$-CONH-B \quad (VII)$$

$$-CON\overset{B}{\underset{B'}{}} \quad (VIII)$$

wherein B and B', which may be the same or different, each represents an aliphatic group containing 1 to 32 carbon atoms, or an aryl group, wherein the alkyl group and the aryl group may be substituted with one or more of a halogen atom, a nitro group, a cyano group, a hydroxy group, a carboxy group, an amino group, an alkyl group, an aryl group, an alkoxycarbonyl group, an acyloxycarbonyl group, an amido group, an imido group, a carbamoyl group, a sulfamoyl group, an alkoxy group, or an aryloxy group; and D and D', which may be the same or different, each represents the groups described for B and additionally an —OB group, an —NH—B group, or an —NB₂ group; R₄, R₅ and R₆, which may be the same or different, each represents a hydrogen atom, a halogen atom, an alkyl group, an aryl group, an alkoxy group, an alkylthio group, a heterocyclic ring, an amino group, a carbonamido group, a sulfonamido group, a sulfamoyl group or a carbamoyl group.

7. The photographic material of claim 5, wherein the coupler is represented by the general formula (IIB):

wherein R and R₁ each has the same meaning as defined in the formula (I); R₃ represents a hydrogen atom, an aliphatic group containing up to 30 carbon atoms, or a carbamoyl group represented by said formulae (VII) or (VIII); R₄, R₅, R₆, R₇ and R₈, which may be the same or different, each represents a hydrogen atom, a halogen atom, an alkyl group, an aryl group, an alkoxy group, an alkylthio group, a heterocyclic ring, an amino group, a carbonamido group, a sulfonamido group, a sulfamoyl group or a carbamoyl group; and W represents a non-metallic atomic group necessary to complete a 5- or 6-membered ring.

8. The photographic material of claim 5, wherein W represents a non-metallic atomic group necessary to complete a benzene ring, a cyclohexene ring, a cyclopentene ring, a thiazole ring, an oxazole ring, an imidazole ring, a pyridine ring or a pyrrole ring.

9. The photographic material of claim 6, wherein W represents a non-metallic atomic group necessary to complete a benzene ring.

10. The photographic material of claim 1, wherein the aliphatic group represented by R may be substituted with a halogen atom or a phenyl group in addition to the sulfonyl group.

11. The photographic material of claim 1, wherein said cyan dye-forming coupler is present in a red-sensitive silver halide emulsion layer.

12. A process for forming a colored image which comprises developing a photographic silver halide light-sensitive material in the presence of a cyan dye-forming colorless photographic coupler wherein the coupling-off position capable of reacting with the oxidized product of an aromatic primary amine developing agent is substituted with at least one alkoxy group substituted with a sulfonyl group as a coupling-off group, said alkoxy group being represented by the formula (I):

wherein R represents a saturated or unsaturated divalent aliphatic group having 1 to 4 carbon atoms which may be straight or branched chain and may be substituted provided that R is not substituted with an aryl group at the α-position; and R₁ represents an aliphatic group, or an aromatic group.

13. A process for forming a colored image which comprises developing a photographic silver halide light-sensitive material in the presence of a cyan dye-forming colorless photographic coupler represented by the general formulae (Ia) or (Ib):

wherein A represents a phenolic or naphtholic group; A' represents a phenolic or naphtholic group; R and R', which may be the same or different, each represents a saturated or unsaturated divalent aliphatic group; $R_1$ represents an alkyl group, an alkenyl group, an aralkyl group, an aralkenyl group, or an aryl group; and n represents a positive integer.

14. The process of claim 12, wherein the alkyl group, the alkenyl group, the aralkyl group, the aralkenyl group, the aryl group and the heterocyclic group represented by $R_1$ may be unsubstituted or substituted with one or more of a halogen atom, a nitro group, a cyano group, a hydroxy group, an alkoxy group, an acyloxy group, an acylamino group, a sulfonamido group, a sulfamoyl group, a sulfonyl group, a carboxy group or a sulfo group.

15. The process of claim 12, wherein the sulfonyl group on the alkoxy group is positioned on the α-, β- or γ-position of the alkoxy group.

16. The process of claim 12, wherein the coupler is represented by the general formulae (IIA) or (IIB):

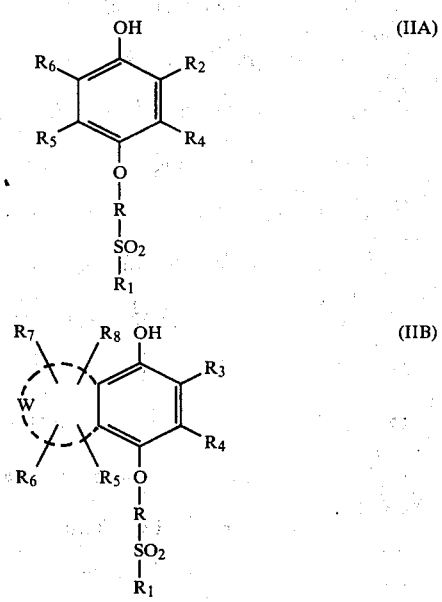

wherein R and $R_1$ each has the same meaning as defined in the formula (I); $R_2$ represents a hydrogen atom, an aliphatic group containing up to 30 carbon atoms, an alkoxy group containing up to 30 carbon atoms, an aryloxy group, an acylamido group, a sulfonamido group, a phosphoramido group, a ureido group, or a carbamyl group, each represented by the general formulae (III) to (VIII):

$$-NH-CO-B \quad \text{(III)}$$

$$-NH-SO_2-B \quad \text{(IV)}$$

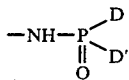

$$-NHCONH-B \quad \text{(VI)}$$

$$-CONH-B \quad \text{(VII)}$$

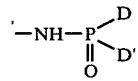

wherein B and B', which may be the same or different, each represents an aliphatic group containing 1 to 32 carbon atoms, or an aryl group, wherein the alkyl group and the aryl group may be substituted with one or more of a halogen atom, a nitro group, a cyano group, a hydroxy group, a carboxy group, an amino group, an alkyl group, an aryl group, an alkoxycarbonyl group, an acyloxycarbonyl group, an amido group, an imido group, a carbamoyl group, a sulfamoyl group, an alkoxy group, or an aryloxy group; and D and D', which may be the same or different, each represents the groups described for B and additionally an —OB group, an —NH—B group, or an —NB$_2$ group; $R_3$ represents a hydrogen atom, an aliphatic group containing up to 30 carbon atoms, or a carbamoyl group represented by said formulae (VII) or (VIII); $R_4$, $R_5$, $R_6$, $R_7$ and $R_8$, which may be the same or different, each represents a hydrogen atom, a halogen atom, an alkyl group, an aryl group, an alkoxy group, an alkylthio group, a heterocyclic ring, an amino group, a carbonamido group, a sulfonamido group, a sulfamoyl group or a carbamoyl group; and W represents a non-metallic atomic group necessary to complete a 5- or 6-membered ring.

17. The process of claim 16, wherein the coupler is represented by the general formula (IIA):

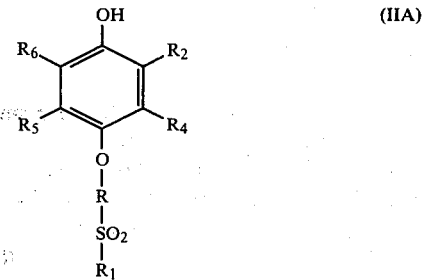

wherein R and $R_1$ each has the same meaning as defined in the formula (I); $R_2$ represents a hydrogen atom, an aliphatic group containing up to 30 carbon atoms, an alkoxy group containing up to 30 carbon atoms, an aryloxy group, an acylamido group, a sulfonamido group, a phosphoramido group, a ureido group or a carbamyl group, each represented by the general formulae (III) to (VIII):

$$-NH-CO-B \quad \text{(III)}$$

$$-NH-SO_2-B \quad \text{(IV)}$$

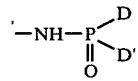

$$-NHCONH-B \quad \text{(VI)}$$

$$-CONH-B \quad \text{(VII)}$$

wherein B and B', which may be the same or different, each represents an aliphatic group containing 1 to 32 carbon atoms, or an aryl group, wherein the alkyl group and the aryl group may be substituted with one or more of a halogen atom, a nitro group, a cyano group, a hydroxy group, a carboxy group, an amino group, an alkyl group, an aryl group, an alkoxycarbonyl group, an acyloxycarbonyl group, an amido group, an imido group, a carbamoyl group, a sulfamoyl group, an alkoxy group, or an aryloxy group; and D and D', which may be the same or different, each represents the groups described for B and additionally an —OB group, an —NH—B group, or an —NB$_2$ group; R$_4$, R$_5$ and R$_6$, which may be the same or different, each represents a hydrogen atom, a halogen atom, an alkyl group, an aryl group, an alkoxy group, an alkylthio group, a heterocyclic ring, an amino group, a carbonamido group, a sulfonamido group, a sulfamoyl group or a carbamoyl group.

18. The process of claim 16, wherein the coupler is represented by the general formula (IIB):

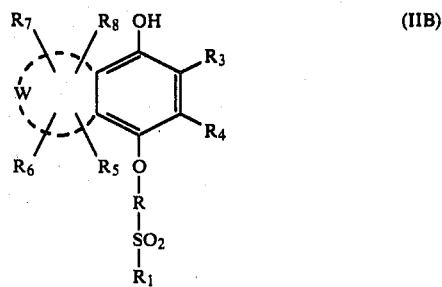

(IIB)

wherein R and R$_1$ each has the same meaning as defined in the formula (I); R$_3$ represents a hydrogen atom, an aliphatic group containing up to 30 carbon atoms, or a carbamoyl group represented by said formulae (VII) or (VIII); R$_4$, R$_5$, R$_6$, R$_7$ and R$_8$, which may be the same or different, each represents a hydrogen atom, a halogen atom, an alkyl group, an aryl group, an alkoxy group, an alkylthio group, a heterocyclic ring, an amino group, a carbonamido group, a sulfonamido group, a sulfamoyl group or a carbamoyl group; and W represents a non-metallic atomic group necessary to complete a 5- or 6-membered ring.

19. The process of claim 16, wherein W represents a non-metallic atomic group necessary to complete a benzene ring, a cyclohexene ring, a cyclopentene ring, a thiazole ring, an oxazole ring, an imidazole ring, a pyridine ring or a pyrrole ring.

20. The process of claim 19, wherein W represents a non-metallic atomic group necessary to complete a benzene ring.

21. The process of claim 12, wherein the aliphatic group represented by R may be substituted with a halogen atom or a phenyl group in addition to the sulfonyl group.

22. The process of claim 12, wherein said cyan dye-forming coupler is present in a red-sensitive silver halide emulsion layer.

23. The photographic material of claim 1 wherein R$_1$ is said aliphatic group.

24. The photographic material of claim 1 wherein R$_1$ is said aromatic group.

25. The photographic material of claim 2 wherein R$_1$ is said alkyl group.

26. The photographic material of claim 2 wherein R$_1$ is said alkenyl group.

27. The photographic material of claim 2 wherein R$_1$ is said aralkyl group.

28. The photographic material of claim 2 wherein R$_1$ is said aralkenyl group.

29. The photographic material of claim 2 wherein R$_1$ is said aryl group.

30. The process of claim 10 wherein R$_1$ is said aliphatic group.

31. The process of claim 10 wherein R$_1$ is said aromatic group.

32. The process of claim 13 wherein R$_1$ is said alkyl group.

33. The process of claim 13 wherein R$_1$ is said alkenyl group.

34. The process of claim 13 wherein R$_1$ is said aralkyl group.

35. The procss of claim 13 wherein R$_1$ is said aralkenyl group.

36. The process claim 13 wherein R$_1$ is said aryl group.

* * * * *